United States Patent [19]
Berry et al.

[11] Patent Number: 5,125,915
[45] Date of Patent: Jun. 30, 1992

[54] LOCKING Y-CONNECTOR FOR SELECTIVE ATTACHMENT TO EXTERIOR OF MEDICAL TUBING

[75] Inventors: Gaylord L. Berry, Salt Lake City; W. Lynn Kerby, Sandy, both of Utah

[73] Assignee: Cardiopulmonics, Inc., Salt Lake City, Utah

[21] Appl. No.: 488,742

[22] Filed: Mar. 2, 1990

[51] Int. Cl.⁵ .................................. A61M 25/00
[52] U.S. Cl. .................................. 604/283; 604/243; 285/147; 285/309
[58] Field of Search ............ 604/26, 43, 165, 171, 604/178, 243, 256, 283, 284, 905; 128/912, DIG. 3; 285/147, 169, 309

[56] References Cited
U.S. PATENT DOCUMENTS

| | | | |
|---|---|---|---|
| 4,187,848 | 2/1980 | Taylor | 604/243 |
| 4,559,043 | 12/1985 | Whitehouse et al. | 604/243 |
| 4,613,329 | 10/1986 | Bodicky | 604/243 |
| 4,842,592 | 6/1989 | Caggiani et al. | 604/283 |
| 4,857,062 | 8/1989 | Russell | 604/905 |
| 4,886,507 | 12/1989 | Patton et al. | 604/284 |

Primary Examiner—John D. Yasko
Assistant Examiner—Anthony Gutowski
Attorney, Agent, or Firm—Workman, Nydegger & Jensen

[57] ABSTRACT

A connector for applying to the exterior of an elongated member of circular cross-section circumferentially uniform radially directed compressive forces by which to effect attachment and fluid-tight sealing thereagainst. The connector comprises an attachment fitting having formed therethrough a bore for slidably receiving the elongated member and a coaxially disposed, radially enlarged compression recess communicating therewith. A flexible annular gripping member resides in the compression recess slidably circling the elongated member. A locking hub disposed at the end of the compression recess remote from the bore has a compression face which extends into compression recess. The locking hub is longitudinally slidable relative to the attachment fitting between a disengaged position in which the elongated member is slidable relative to the gripping member and an engaged position in which the compression face bears against and deforms the gripping member to preclude sliding of the tubing relative to the gripping member by urging the gripping member into radial engagement with the portion of the tubing in the compression recess. A retention pin and cooperating retention slot on opposed portions of attachment fitting and the locking hub secure the locking hub in its engaged position. The connector has specific utility in terminating the proximal end of a coaxial lumen tube assembly used to interconnect an implanted extrapulmonary blood gas exchange device with extracorporeal support equipment.

68 Claims, 5 Drawing Sheets

LOCKING Y-CONNECTOR FOR SELECTIVE ATTACHMENT TO EXTERIOR OF MEDICAL TUBING

BACKGROUND

1. The Field of the Invention

This invention relates to devices for selectively attaching a fixture to the exterior of an elongated member of circular cross-section, such as a length of medical tubing. More specifically, the invention pertains to a connector for effecting a fluid-tight termination of the outer lumen of a coaxial lumen tube assembly against the inner lumen tube of that assembly. The invention has particular utility at the proximal end of a coaxial lumen tube assembly used with an implanted extrapulmonary blood gas exchange device to enable that device to communicate with extracorporeal support equipment.

2. BACKGROUND ART

Disclosed in U.S. Pat. Nos. 4,583,969 and 4,850,958 are methods an apparatus for the in vivo oxygenation of blood without using or disturbing the lungs of the patient. A longitudinal bundle of elongated, gas-permeable capillary tubes bound are together at the ends and inserted into the vena cava through an incision made at a remote site in the circulatory system, such as the femoral or iliac vein.

In the embodiment of the apparatus disclosed in U.S. Pat. No. 4,850,958, a coaxial lumen tube assembly is used to establish the inward and outward gas flow required between extracorporeal support equipment and the implanted bundle. A feed gas, rich in oxygen, is supplied through one lumen of the coaxial lumen tube assembly to the proximal end of the bundle of capillary tubes. The feed gas passes through the capillary tubes and is exchanged through the walls thereof for metabolic byproducts in the blood circulating in the aorta about the exterior of the capillary tubes. At the distal ends of the capillary tubes, the gas is removed through the other lumen of the coaxial lumen tube assembly. In the particular embodiment of the apparatus disclosed, fresh oxygen-bearing feed gas is supplied to the implanted device through the central lumen of the coaxial lumen tube assembly, while exhausted gas is removed through the surrounding outer lumen.

Outside of the body of the patient, the inner and outer lumen tubes of the coaxial lumen tube assembly must become separated, to permit their connection individually to different equipment. The inner lumen tube is connected to a source of the pressurized feed gas; the outer lumen is connected to a vacuum. At a point where the flow paths of the coaxial lumen tube assembly branch, it is necessary to terminate the outer lumen tube in a fluid-tight seal against the inner lumen tube. In the past, efforts to effect these functions at the branching point of the two flow paths has focused without full success on various Y-connector configurations. The constraints on such Y-connectors imposed by the surgical procedures associated with the implantation and use of the blood gas exchange device have resulted in structural demands which have yet to be satisfied.

It is necessary, for example, during the implantation procedure of the blood gas exchange device for the proximal terminus of the outer lumen of the dual-lumen assembly to be free of any Y-connector. After implantation is complete, the Y-connector is slid down the inner lumen tube to the proximal terminus of the outer lumen tube and secured in place. The sealing engagement between the Y-connector and the outer lumen tube may be effected by a number of known structures. The required slidable sealing engagement between the Y-connector and the inner lumen tube has, by contrast, presented a challenge to achieve.

In order to effect a fluid-tight seal by which to terminate the outer lumen tube against the inner lumen tube, it is necessary to effect an unbroken contact about the entire circumference of the outer surface of the inner lumen tube. To do so, a structure is required that will impose radially directed forces against the exterior of the inner lumen tube in a manner that is circumferentially uniform. If the radial forces are not circumferentially uniform, grave consequences may result. The fluid-tight seal may be compromised, or the shape of the inner lumen tube may become distorted, leading to crimping and constricted fluid flow.

The desired fluid-tight seal must be capable of being repeatedly applied and released. The fact that the seal imposed must be released and reapplied only serves to emphasize the need to develop radially directed forces against the exterior of the inner lumen tube which are circumferentially uniform. If the shape of the inner lumen tube is distorted by the application of these forces, an acceptable seal might result in the first instance. Nevertheless, after the release of the seal and its reapplication, possibly at a different longitudinal location or in a manner radially displaced from the initial application, a secure seal will be difficult to guarantee. Furthermore, the sealing elements involved must be both resilient and extremely durable. Thus, the sealing force to be effected must be capable of repeated actuation without degrading the structural integrity of the Y-connection or the inner lumen tube.

The Y-connector seal must also be one that releases only when intended. Accidental or creeping release of the seal, such as occurs in prior devices that secure the seal using threaded fittings, are undesirable. On the other hand, the seal must be capable of rapid and certain disengagement.

Finally, it is of concern that the coupling mechanisms associated with the Y-connector be easily assemblable, that the Y-connector be repeatedly slidable over the inner lumen tube without damage to either component, and that the manner of operating the mechanisms associated with the Y-connector be unambiguous to surgical personnel.

In the broader context, the problem of effecting a fluid-tight seal in the context just described is the problem of providing a connector for effecting the selective, reliable, and reversible attachment of a fitting to the exterior of an elongated member of circular cross-section. Where the elongated member is a length of medical tubing, the apparatus for effecting the desired connection must embody a combination of firm, yet not overpowering, compressive forces. Once this balance has been achieved, the compressive forces can be utilized on behalf of a fluid-tight seal or merely a mechanical attachment, as for example with the attachment to an I.V. tube of a label, a monitor, or a reserve piece of equipment.

In the context of an in vivo extrapulmonary blood gas exchange device, such as that described in U.S. Pat. No. 4,850,958, the general principles by which such an object is achieved take on specific detailed form. While that specific detailed form will be disclosed hereafter in a discussion of the invention, it should be understood that the principles embodied therein have a wide range of applicability without departing from the broad insights that constitute that invention.

BRIEF SUMMARY AND OBJECTS OF THE INVENTION

Accordingly one object of the present invention is to provide a connector for the exterior of an elongated member which is slidable along the length thereof and which may be secured at any selected location without damaging the elongated member.

Another object of the present invention is to provide such a slidable connector as is capable of effecting a fluid-tight seal against the elongated member.

Still another object of the present invention is a slidable connector as described above which may be used with an extrapulmonary blood gas exchange device to terminate and reliably seal against the inner lumen tube of a coaxial lumen tube assembly the outer lumen tube of that assembly. It is through such a dual lumen assembly that an in vivo extrapulmonary blood gas exchange devices of the type contemplated communicates with extracorporeal support equipment.

Further in that context, it is an object of the present invention that the slidable connector provided include a branching port by which to divert the fluid flow paths of the inner and outer lumen tubes of the dual lumen assembly.

Yet another object of the present invention is a slidable Y-connector as described above that is easy to operate and reliably releasable on a repeated basis.

A further object of the present invention is to produce a Y-connector as described above that will not damage the structure of the elongated member to which it is secured or impede the flow of fluid therethrough.

An additional object of the present invention is a slidable Y-connector that is susceptible to rapid, sure operation, but which will not loosen accidentally.

To achieve the foregoing objects and in accordance with the invention as embodied and broadly described herein, a connector is provided for attaching an auxiliary fixture, such as a cap portion for the outer lumen of a coaxial lumen tube assembly, to the exterior of a length of medical tubing, such as the inner lumen tube of such a lumen tube assembly. The connector comprises an attachment fitting to which the fixture is secured and through which is formed a bore sized to slidably receive a portion of the length of the tubing. A compression recess is formed in the attachment fitting which for reference purposes has opposed first and second ends.

The compression recess is disposed in coaxial alignment with the bore, which communicates with the compression recess at its first end. The compression recess is provided between its first and second ends with sidewalls that are radially enlarged relative to those of the bore. The sidewalls encircle a portion of the length of the tubing which is distinct from that portion received in the bore itself and first end of the compression recess tapers from the sidewalls to the bore.

The connector further comprises a resilient, annular gripping member which is housed in the compression recess and configured to encircle the portion of the tubing therein. For ease of reference, the gripping member has a lead end which is disposed adjacent to the first end of the compression recess and a trailing end which is disposed adjacent to the second end of the recess. The edge of the leading end of the gripping member is beveled on the outer radial surface and may optionally be beveled on the inner surface as well. In one embodiment, the gripping member is comprised of rubber and more preferably of a medical grade silicone rubber having a Shore A durometer hardness in the range of from about 25 to about 50. Preferably, the gripping member has a Shore A durometer hardness in the range of about 25 to about 40, or more preferably from about 30 to about 35.

The connector also includes a locking hub that encircles the tubing at the second end of the compression recess. The locking hub has a compression face that projects to the compression recess from the second end thereof. The locking longitudinally in relation to the attachment hub is movable fitting between a disengaged and an engaged position. In the disengaged position the tubing is slidable relative to the gripping member. In the engaged position, however, the compression face bears against and deforms the gripping member to preclude sliding of the tubing relative to the gripping member by urging the gripping member into radial engagement with the portion of the tubing in the compression recess. In the process, a fluid-tight seal is achieved on the exterior of the tubing. In some embodiments a portion of the leading end of the gripping member is extruded into the bore from the compression recess at the first end thereof to enhance the fluid-tight seal.

For the purpose of securely restraining the locking hub in its engaged position, the connector includes a cooperating means located on opposed portions of the attachment fitting and the locking hub for securing the locking hub in its engaged position with the compression face bearing against and deforming the compression member. By way of example, such a cooperating means may include a retention pin located on the exterior of the attachment fitting and a retention slot formed in a sleeve of the locking hub that overlies the retention pin. The retention slot is configured to receive the retention pin when the locking hub is in its engaged position and to do so due to rotation of the locking hub relative to the attachment fitting.

The retention slot is of such a configuration that the entry of the retention pin thereinto simultaneously causes longitudinal movement of the locking hub parallel to the longitudinal axis of the bore in such a direction as to advance the compression face into the compression recess to bear against and deform the compression member. The entrance to the retention slot may be provided with a resilient finger which must be temporarily deformed to admit the retention pin. Thereafter the resilient finger assists in positively constraining the retention pin in the retention slot, and thus in ensuring that the attachment hub remains in its engaged position causing the compression member to seal against tubing.

An associated method for selectively attaching a fixture to the exterior of a length of medical tubing is also within the contemplated scope of the present invention.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENT

Figure 1:
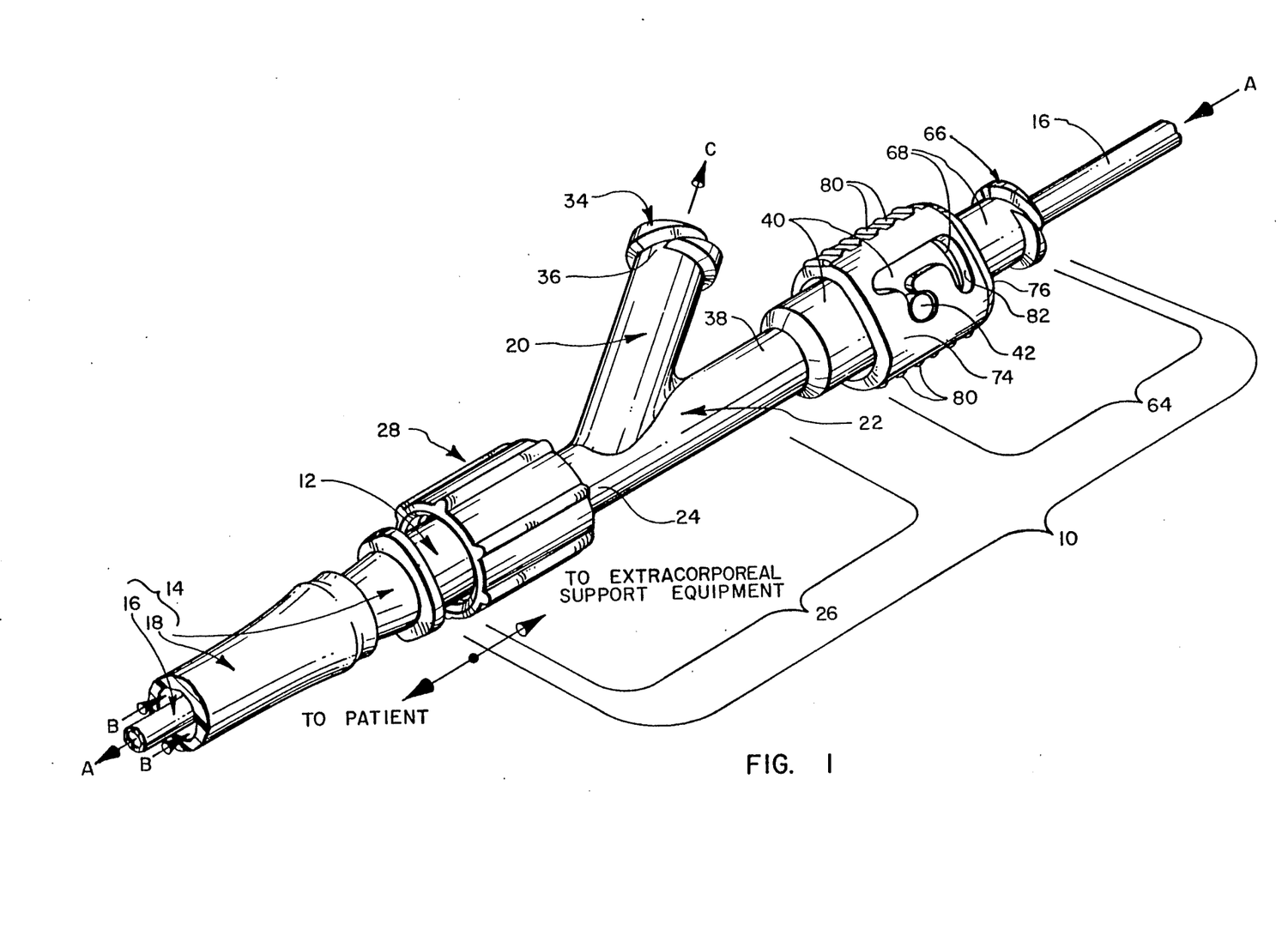
FIG. 1 is a perspective view of a Y-connector incorporating principles of the present invention and employed as part of a system for in vivo extrapulmonary blood gas exchange.

FIG. 1 illustrates a connector configured according to the present invention and utilized as an element of an implantable extrapulmonary blood gas exchange system. Because of the specialized nature of the environment involved, the inventive connector in FIG. 1 takes the form of a Y-connector 10 installed at the proximal end 12 of a coaxial lumen tube assembly 14 which is utilized to communicate between an implanted extrapulmonary blood gas exchange device (not shown) and extracorporeal support equipment (also not shown) Lumen tube assembly 14 includes an inner lumen tube 16 coaxially disposed within an outer lumen tube 18. While outer lumen tube 18 terminates at proximal end 12 of lumen tube assembly 14, inner lumen tube 16 extends therebeyond through Y-connector 10.

A feed gas, rich in oxygen, is fed through inner lumen tube 16 to the implanted blood gas exchange device in a direction shown in FIG. 1 by Arrows A. By passing through the implanted blood gas exchange device, the feed gas become depleted of oxygen and enriched with metabolic byproducts. Thus, gas flowing through the extrapulmonary blood gas exchange system becomes exhaust gas which is then withdrawn from the implanted blood gas exchange device through outer lumen tube 18 in the direction shown in Arrows B. At Y-connector 10, the flow of exhaust gases is diverted from the flow path of inner lumen tube 16 in the direction shown by Arrow C.

Y-connector 10 in this environment serves two functions. First, outer lumen tube 18 is sealingly terminated against the exterior of inner lumen tube 16. Secondly, the fluid flow from outer lumen tube 18 is diverted from the flow path of inner lumen tube 16 through a side port 20. To accomplish these objectives, Y-connector 10 includes two major components which are visible in FIG. 1 and a third which is shown in the exploded view of FIG. 2.

Y-connector 10 comprises an attachment fitting 22 integrally formed with side port 20. The distal end 24 of attachment fitting 22 is provided with a cap portion 26 that includes both side port 20 and a means for sealingly connecting cap portion 26 to the outer lumen 18 of lumen tube assembly 14. By way of example, such a means for sealingly connecting cap portion 26 appears in FIGS. 1 and 2 in the form of a rotatable lock nut fitting 28 on distal end 24 of attachment fitting 22 and a cooperating nonrotatable male taper lock fitting 30, shown in FIG. 2, on proximal end 12 of lumen tube assembly 14. More specifically, female taper lock fitting 30 is located at the terminus 32 of outer lumen tube 18. A similar female luer lock fitting 34 is located at the free end 36 of side port 20 for use in coupling fluid flow diverted therethrough to appropriate extracorporeal support equipment.

Figure 2:
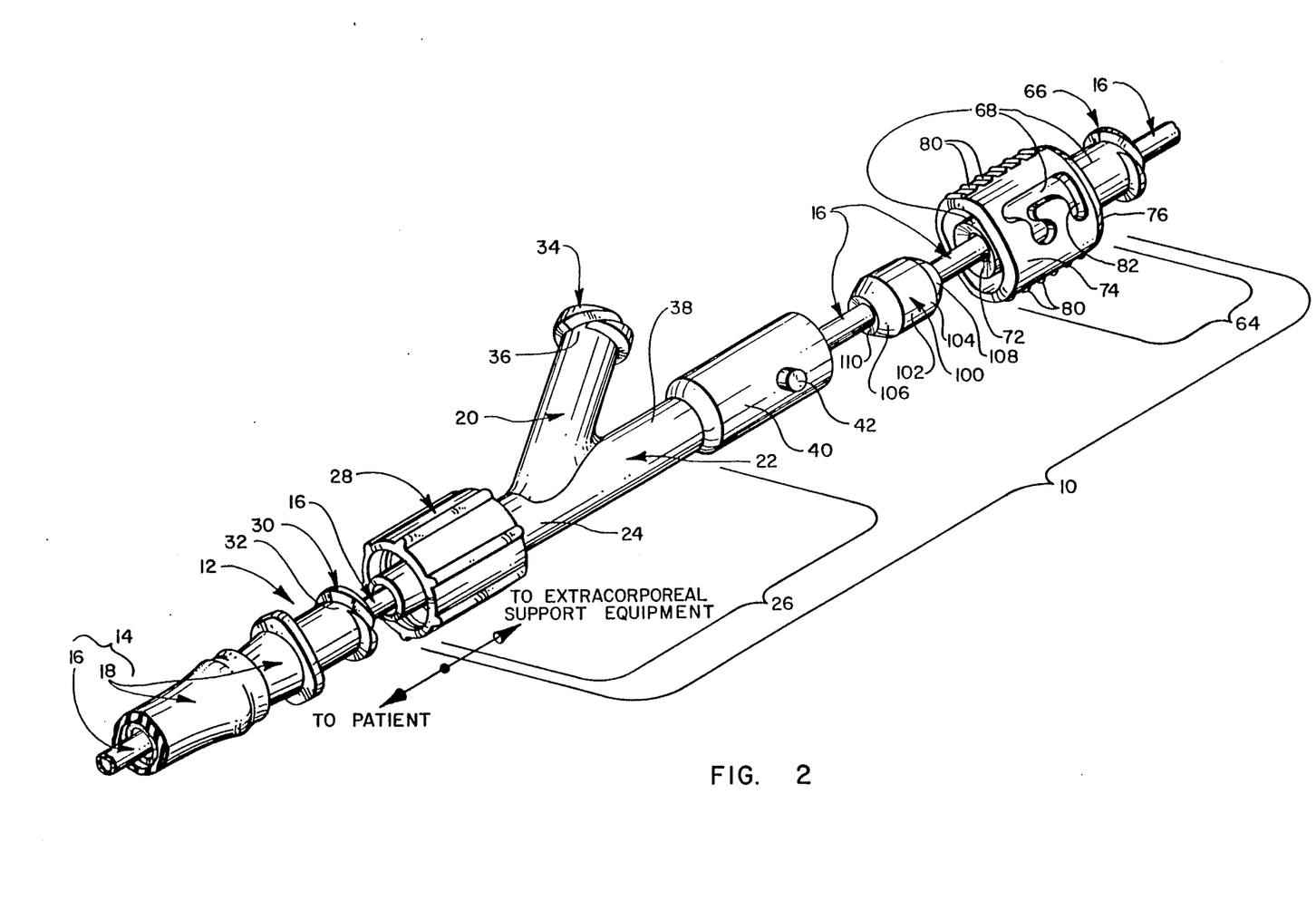
FIG. 2 is an exploded perspective view of the Y-connector shown in FIG. 1.

At proximal end 38, attachment fitting 22 is formed into an enlarged housing 40 which carries on the outer surface thereof an upstanding retention pin 42, the function of which will be explored in detail subsequently.

Figure 3:
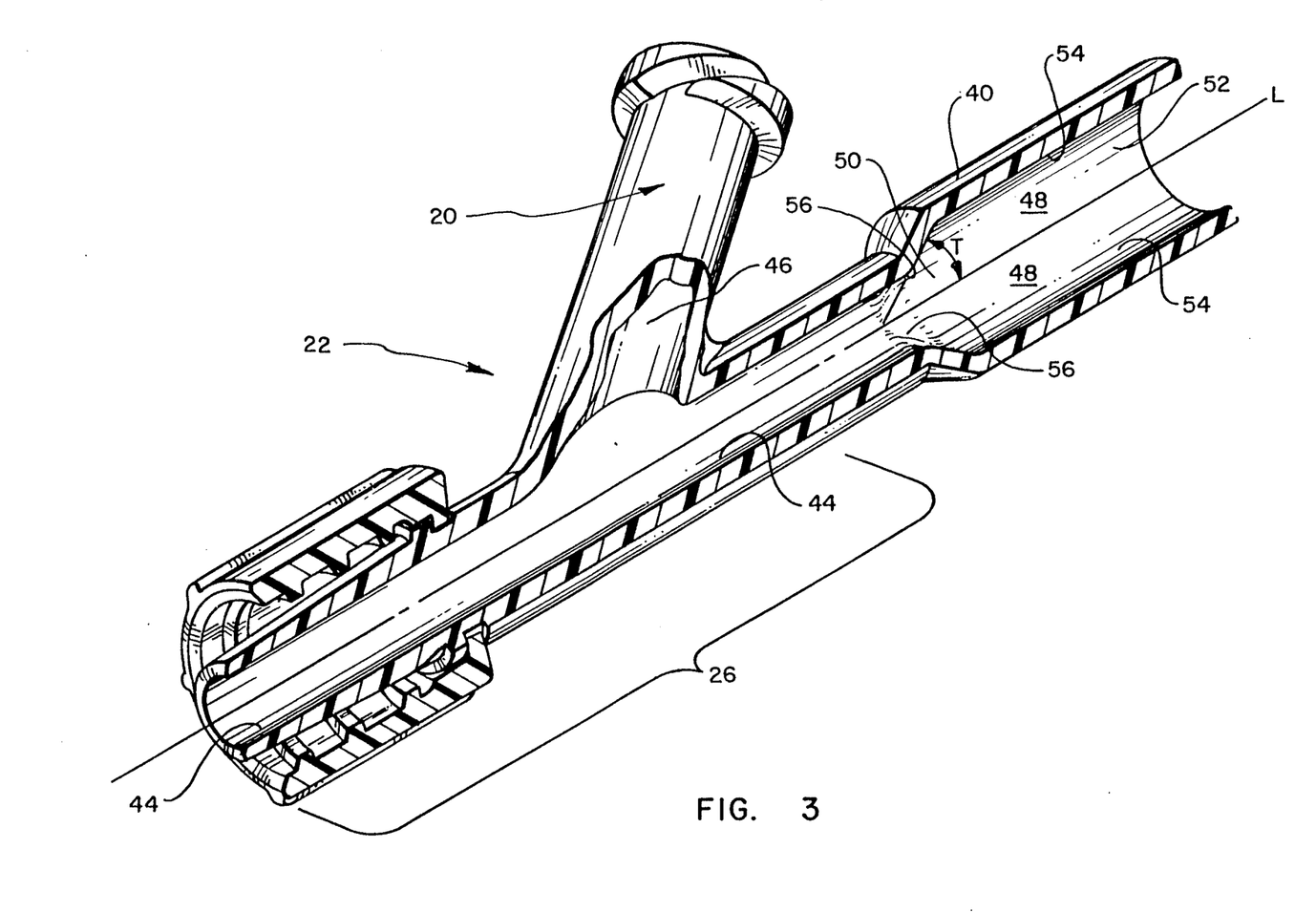
FIG. 3 is a perspective break-away view of the internal structures of the attachment fitting of the connector shown in FIG. 1.

Formed within attachment fitting 22 are internal structures best understood by reference to FIG. 3. Longitudinally formed through attachment fitting 22 at the center thereof is a bore 44 sized to slidably receive inner lumen 16 (not shown). Branching from bore 44 within cap portion 26 is a gas discharge passageway 46 formed longitudinally through side port 20.

Within housing 40 of attachment fitting 22 is formed a compression recess 48 having for reference purposes a first end 50 and a second end 52. Compression recess 48 communicates at first end 50 thereof with bore 44 and is disposed in coaxial alignment therewith. Between first end 50 and second end 52 compression recess 48 has sidewalls 54 that are radially enlarged relative to bore 44 and configured to encircle a portion of the length of inner lumen tube 16 distinct from the portion thereof that is received in bore 44. First end 50 of compression recess 48 tapers from sidewalls 54 thereof at a predetermined angle T to the longitudinal axis L of bore 44. Nevertheless, the juncture 56 between first end 50 of compression recess 48 and bore 44 is for reasons that will become apparent presently, a smooth curving surface.

As shown in both FIGS. 1 and 2, Y-connector 10 further includes a locking hub 64, which in the assembled view of Y-connector 10 shown in FIG. 1 is positioned encircling inner lumen tube 16 at proximal end 38 of attachment fitting 22. Locking hub 64 comprises a cylindrical body portion 68 having formed on the end thereof remote from attachment fitting 22 a female taper lock fitting 66. As seen in FIG. 2, the end of body portion 68 adjacent to attachment fitting 22 terminates in an annular compression face 72 that is inclined toward attachment fitting 22 relative to the longitudinal axis of bore 44.

Locking hub 64 further comprises a retention sleeve 74 disposed in a generally coaxial relationship with body portion 68 of locking hubs 64. The proximal end 76 of retention sleeve 74 is secured to body portion 68. Distal end 78 of retention sleeve 74, however, is configured so as to overlie housing 40 of attachment fitting 22 with body portion 68 of locking hub 64 extending into housing 40 when the components of Y-connector 10 are in the assembled relationship shown in FIG. 1. The relationship of these internal structures is shown more clearly in FIGS. 5 and 7. The interaction of body portion 68 with other structural elements of Y-connector 10 located in housing 40 will be discussed subsequently.

Formed on the exterior of opposite sides of retention sleeve 74 are a series of ridges 80 comprising a gripping surface by which surgical personnel can secure Y-connector 10 in position at proximal end 12 of lumen tube assembly 14. Formed through retention sleeve 74, so as to communicate with the annular space between body portion 68 and retention sleeve 74 is a patterned recess 82, which in the assembled state of Y-connector 10 shown in FIG. 1 interacts with retention pin 42 toward the end of securing the seal effected by Y-connector 10.

Figure 4:
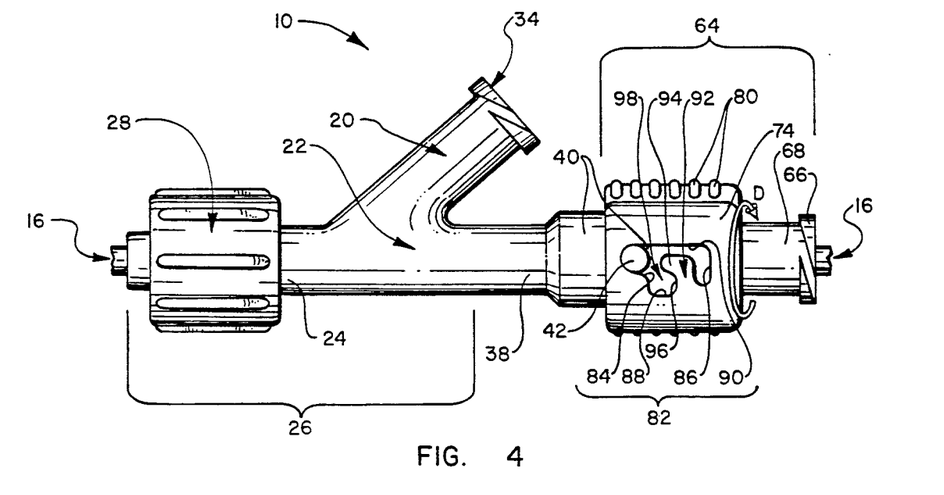
FIG. 4 is an enlarged elevation view of the Y-connector of FIG. 1 with the locking hub in the disengaged position thereof.
Figure 6:
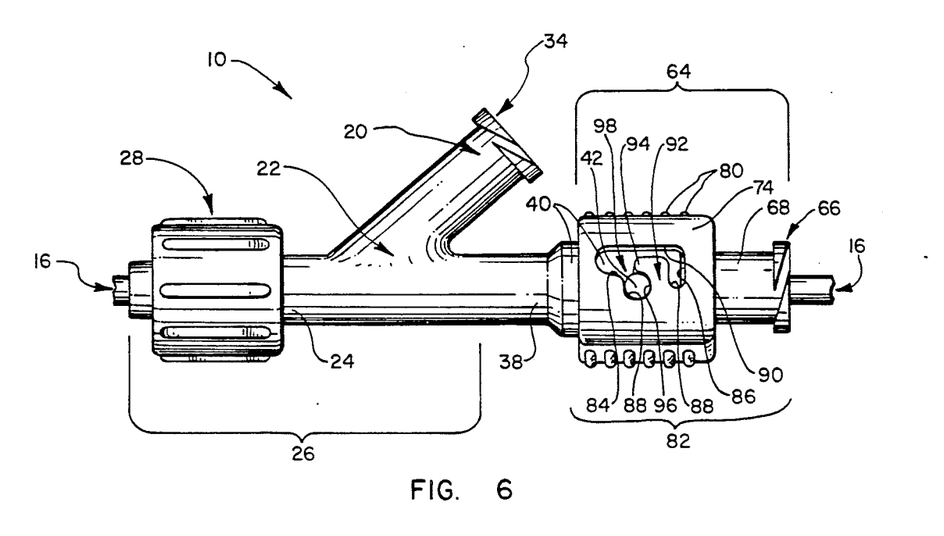
FIG. 6 is an enlarged elevation view of the Y-connector in FIG. 1 with the locking hub in the engaged position thereof.

The precise structure of pattern recess 82 is best disclosed relative to FIGS. 4 and 6, where recess 82 is seen to be bounded by a front edge 84, a rear edge 86, and opposed longitudinal edges 88, 90, which are generally parallel to the longitudinal axis of Y-connector 10. Projecting into patterned recess 82 from and generally normal to lateral edge 88 is a finger 92. Finger 92 terminates in an enlarged knob 94 which is directed from lead edge 96 of finger 92 toward front edge 84 of patterned recess 82. In this manner, formed between lead edge 96 of finger 92 and front edge 84 is a retention slot 98 which communicates with patterned recess 82 and terminates at longitudinal edge 88 thereof. The entrance to retention slot 98 is partially closed by knob 94 on retention finger 92. By virtue of the thickness of retention sleeve 74 and the nature of the material of which it is comprised, finger 92 is resiliently deformable away from front edge 84 of patterned recess 82, whereby the entrance to retention slot 98 can be widened temporarily.

In the placement of Y-connector 10 in position at proximal end 12 of lumen tube assembly 14, retention pin 42 and patterned recess 82 interact to ensure that the sealing engagement made by Y-connector 10 with the exterior of inner lumen tube 16 is certain and secure until intentionally released by medical personnel. A full appreciation of how this sealing engagements is affected requires a discussion of a third major component of Y-connector 10.

As seen in FIG. 2, Y-connector 10 further comprises a resilient annular gripping member 100 which is sized so as to slidably encircle inner lumen tube 16 of lumen tube assembly 14. In the assembled state of Y-connector 10 gripping member 80 is interposed between locking hub 64 and attachment fitting 22 resting within compression recess 48.

It is through the medium of gripping member 100 that Y-connector 10 is able to effect a radially directed circumferentially uniform press of force against the exterior of inner lumen tube 16 in a selective, repeatable manner. Gripping member 100, thus actually effects the fluid tight termination of outer lumen tube 18 against inner lumen tube 16.

When assembled as a component of Y-connector 10, gripping member 100 can for ease of reference be said to have a lead end 102 on the side thereof adjacent to attachment fitting 22 and a trailing end 104 at the side thereof closest to locking hub 64. As shown in FIG. 2, lead end 102 of gripping member 100 is provided on the outer radial surface thereof with a lead beveled surface 106. Similarly, trailing end 104 of gripping member 100 is provided on the outer radial surface thereof with a trailing bevel surface 108. As will be appreciated by reference to the cross-sectional views shown in FIGS. 5 and 7, the inclination of lead bevel surface 106 corresponds to angle T shown in FIG. 3 at which first end 50 of compression recess 48 necessarily tapers relative to the longitudinal axis L of bore 44. Correspondingly, the inclination of trailing beveled surface 108 corresponds to the inclination of compression face 72 on body portion 68 of locking hub 64.

In addition, lead end 102 of gripping member 100 has an internal bevel surface 110 on the inner radial surface thereof which assists in positioning Y-connector 10 at proximal end 12 of lumen tube assembly 14 by facilitating sliding Y-connector 10 down inner lumen 16 thereof. Optionally such an inner bevel surface can also be provided on the inner radial surface of trailing end 104.

Preferably, gripping member 100 is comprised of a durable but resilient material, such as natural or medical grade silicone rubber, or a thermoplastic elastomer, such as Krayton$_{TM}$ or C-flex$_{TM}$. In order to perform its intended function as a component of Y-connector 10, the material of which gripping member 100 is formed should have a Shore-A durometer range of from about 25 to about 50. Softer materials tend to lose their physical integrity with use, and for their lack of resiliency do not permit rapid and repeated disengagement of Y-connector from the outer surface of inner lumen tube 16. At the other extreme, harder materials provide too much resistance in effecting sealing engagement against the outside of inner lumen tube 16. More specifically, a Shore-A durometer hardness in the range from about 25 to about 40 is desirable, while a Shore-A durometer hardness range of from about 30 to about 35 has been demonstrated to be optimally successful.

As disposed at proximal end 38 of attachment fitting 22, locking hub 64 is movable longitudinally relative to attachment fitting 22 between a disengaged position and an engaged position. In the disengaged position which is shown in FIGS. 4 and 5, Y-connector 10 is slidable relative to the lumen tube 16 that is passed through gripping member 100.

Figure 5:
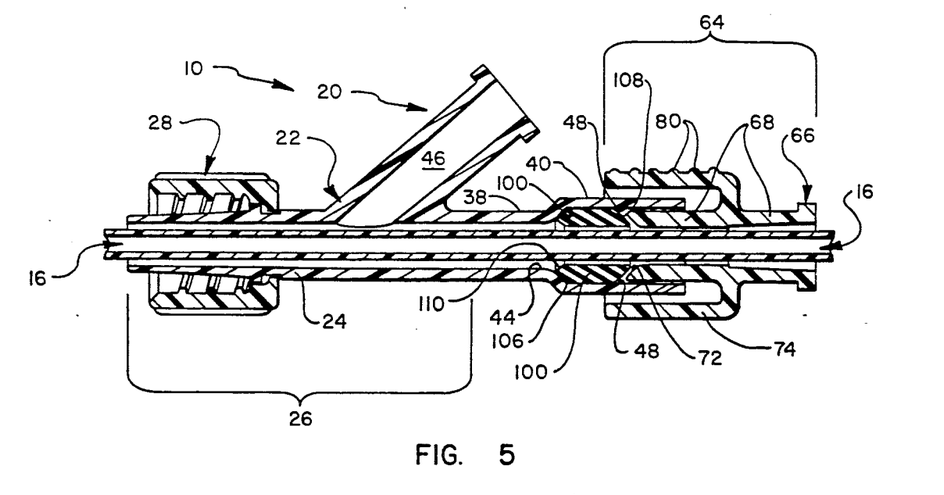
FIG. 5 is a cross-section elevational view of the Y-connector as in FIG. 4.

In the disengaged position, which is shown in FIGS. 4 and 5, retention pin 42 is in patterned recess 82 out of retension slot 98. Although body portion 68 of locking hub 64 extends into compression recess 48, compression face 72 thereof does not engage trailing bevel surface 108 of gripping member 100, or if such engagement occurs, the force of compression face 72 upon gripping member 100 is minimal at most. Locking hub 64 is also rotatable relative to attachment fitting 22.

Figure 7:
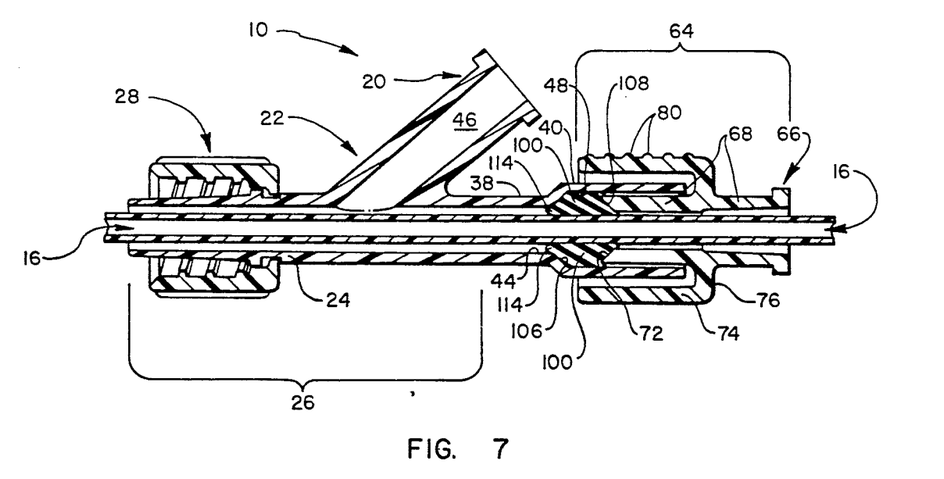
FIG. 7 is a cross-sectional elevation view of the Y-connector shown in FIG. 6.

In the engaged position of locking hub 64, however, compression face 72 bears against trailing bevel surface 108 of gripping member 100 and deforms gripping member 100 toward the end of precluding sliding of inner lumen tube 16 relative to gripping member 100. As shown in FIGS. 6 and 7, gripping member 100 is urged into radial engagement with the portion of inner lumen tube 16 within compression recess 48. A gripping member 100 made of the materials described above, and exhibiting the hardness disclosed, deforms in the face of pressure from compression face 72 as to transfer radially directed circumferentially uniform compressive forces against the outside of inner lumen tube 16.

It has been found particularly useful in effecting a sealing engagement with inner lumen tube 16 to fabricate gripping member 100 of such a material as allows a portion of lead end 102 of gripping member 100 to extrude into bore 44 when this occurs. Such a relationship among the elements of Y-connector 10 is shown in FIG. 7, where portion 114 of the member 100 has been extruded into bore 44. Nevertheless, the physical nature of gripping member 100 must be such that upon the release of pressure by compression surface 72, gripping member 100 readily resumes it former shape by drawing portion 114 from bore 44 and releasing the radially directed compressive force previously exerted on the exterior of inner lumen tube 16.

Conforming the inclination of lead bevel surface 106 to that of first end 50 of compression recess 48 has been found to assist in the process of converting compressive forces exercised on gripping member 100 into forces radially directed against the outside of inner lumen tube 16. The juncture 56 between first end 50 of compression recess 48 and bore 44 is necessarily made free of sharp edges in order to avoid causing damage to the lead end 102 of gripping member 100 when portion 114 of thereof is extruded into bore 44. Similarly, forming gripping member 100 so that trailing bevel surface 108 thereof conforms in inclination to that of compression surface 72 facilitates the application of compressive forces to gripping member 100 and their translation into radially directed gripping forces on inner lumen tube 16 without causing damage to the structural integrity of gripping member 100.

According to yet another aspect of the invention, a connector, such as Y-connector 10, comprises cooperating means located on opposing portions of attachment fitting 22 and locking hub 64 for selectively locking hub 64 in the engaged position thereof. In this manner, once gripping member 100 is placed in compression by movement of locking hub 64 into the engaged position thereof, locking hub 64 will remain in that position and gripping member 100 will remain in compression effecting a fluid-type seal against inner lumen tube 16 until such time as locking hub 64 is intentionally released from its engaged position.

As shown by way of example and not limitation in FIGS. 4 and 6, retention pin 42 on the exterior surface of housing 40 and patterned recess 82 formed through retention sleeve 74 perform this function. In the disengaged position of locking hub 64 shown in FIG. 4, retention pin 42 rests in a forward portion of patterned recess 82 out of retention slot 98. Advantageously, front edge 84 of patterned recess 82 is so configured as to permit retention pin 42 to be entered into retention slot 98 through movement of locking hub 64 relative to attachment fitting 28, and specifically due exclusively to the rotation of locking hub 64 relative to attachment fitting 22 in the direction shown by Arrow D. In the process, locking hub 64 is automatically advanced longitudinally toward attachment fitting 22 without the exercise of longitudinally directed forces by surgical personnel due to the coming action of front edge 84 and retention pin 92.

Retention pin 42 is positively retained in retention slot 98 by the action of resilient finger 92 and knob 94 at the free end thereof. Knob 94 serves to narrow the entrance to retention slot 98, so that the entry of retention pin 42 thereinto requires the displacement of flexible finger 92 away from front edge 84 of patterned recess 82. Once retention pin 42 has passed beyond knob 94 into retention slot 84, however, resilient finger 92 resumes its former position with knob 94 again narrowing the entrance to retention slot 98. This relationship among the components is shown in FIG. 6 and constitutes the position of locking hub 64 in the engaged position thereof. Knob 94 by partially closing the entrance to retention slot 98 thus serves to positively retain locking hub 64 in its engaged position and is shown in FIG. 7, gripping member 100 is simultaneously maintained in a deformed state radially urged against the exterior of inner lumen tube 16. The positive retention of retaining pin 92 in retention slot 98 provides a significant safety feature to Y-connector 10, in that accidental disengagement of locking hub 64 cannot occur.

Thus, a connector has been disclosed which reliably and repeatedly can effect a secure engagement the exterior surface of an elongated member of circular cross-section, such as a length of medical tubing. The shape and specific resiliency disclosed as being provided in the sealing member of the connector affords optimal operation by permitting the engagement to be made without degrading either the elongated circular tubing or the elements of the connector itself. Retention pin 42 and the shape of patterned recess 82 permit the placement of the gripping member into compression merely by the exertion of rotational forces upon the locking hub of the device. Thus, excessive longitudinal forces of compression are never applied to the critical gripping member of the invention. In addition, the specific configuration of patterned recess 82 relative to retention pin 42 permits locking hub 64 to be securely set in the engaged position thereof, effecting a fluid tight seal against the outside of inner lumen tube 16 which is not releasable until such a result is intentionally desired by medical personnel.

The inventive device has potential application in a number of fields for securing articles or fittings to the outside of elongated members. A corresponding method for securing the article or fitting to an elongated member is within the scope of the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A connector for selective attachment to the exterior of an elongated member of circular cross-section, said connector comprising:
   a. An attachment fitting having formed therethrough a bore sized to slidably receive a portion of the length of the elongated member;
   b. a compression recess formed in said attachment fitting having opposed first and second ends, said bore communicating with said first end of said compression recess and being disposed in coaxial alignment therewith, said compression recess between said first and second ends thereof having sidewalls enlarged radially relative to said bore and configured to encircle a portion of the length of the elongated member distinct from the portion thereof received in the bore;
   c. a resilient, annular gripping member housed in said compression recess and configured to encircle the portion of the elongated member therein;
   d. a locking hub configured for encircling the elongated member at said second end of said compression recess and having a compression face projecting into said compression recess from said second end thereof, said locking hub being movable longitudinally relative said attachment fitting between a disengaged position in which the elongated member is slidable relative to said gripping member and an engaged position in which said compression face bears against and deforms said gripping member to preclude sliding of the elongated member relative said gripping member by urging said gripping member into radial engagement with the portion of the elongated member in said compression recess; and e. cooperating means located on opposing portions of said attachment fitting and said locking hub for selectively locking said locking hub in said engaged position thereof, and wherein said cooperating means comprises a retention pin and a retention slot configured to receive said retention pin in said engaged position of said locking hub, said retention pin entering said retention slot due to relative movement between said locking hub and said attachment fitting as said locking hub moves from said disengaged to said engaged position thereof.

2. A connector as recited in claim 1, wherein said first end of said compression recess tapers from said sidewalls thereof to said bore.

3. A connector as recited in claim 2, wherein the juncture between said first end of said compression recess and said bore is a smooth, curving surface.

4. A connector as recited in claim 1, wherein said gripping member is comprised of rubber.

5. A connector as recited in claim 4, wherein said gripping member is comprised of medical grade silicone rubber.

6. A connector as recited in claim 1, wherein said gripping member is comprised of a thermoplastic elastomer.

7. A connector as recited in claim 1, wherein a portion of said gripping member adjacent to said first end of said compression recess is extruded into said bore when said locking hub is in said engaged position thereof.

8. A connector as recited in claim 1, wherein said gripping member has a lead end disposed adjacent said first end of said compression recess and a trailing end disposed adjacent said second end of said compression recess, and wherein the edge of said lead end of said gripping member is beveled on the outer radial surface thereof.

9. A connector as recited in claim 8, wherein the edge of said trailing end of said gripping member is beveled on the outer radial surface thereof.

10. A connector as recited in claim 9, wherein said compression face on said locking hub is inclined relative to the longitudinal axis of said bore at an angle corresponding to the angle of the bevel on the outer radial surface of said edge of said trailing end of said gripping member.

11. A connector as recited in claim 1, wherein said gripping member has a lead end disposed adjacent said first end of said compression recess and a trailing end disposed adjacent said second end of said compression recess; wherein the edge of said lead and said trailing ends of said gripping member are beveled on the outer radial surfaces thereof; wherein said first end of said compression recess tapers from said sidewalls thereof to said bore at an angle to the longitudinal axis of said bore corresponding to the angle of the bevel on the outer radial surface of said edge of said lead end of said gripping member; and wherein said compression face on said locking hub is inclined relative to the longitudinal axis of said bore at an angle corresponding to the angle of the bevel on the outer radial surface of said edge of said trailing end of said gripping member.

12. A connector as recited in claim 11, wherein the inner radial surface of at least one end of said gripping member is beveled.

13. A connector as recited in claim 1, wherein said locking hub is secured to said attachment fitting.

14. A connector as recited in claim 13, wherein said locking hub is capable of rotation about the longitudinal axis of said bore.

15. A connector a recited in claim 1, wherein rotation of said locking hub causes said retention pin to enter said retention slot, and entry of said retention pin into said retention slot advances said locking hub longitudinally relative said attachment fitting, thereby to advance said compression face into aid compression recess from said second end thereof.

16. A connector as recited in claim 1, wherein a resilient finger adjacent to said retention slot partially closes the entry thereinto, thereby in said engaged position of said locking hub to positively retain said retention pin in said retention slot.

17. A connector as recited in claim 1, wherein said retention pin is formed on portion of the exterior of said attachment fitting, and said retention slot is formed in a cuff of said locking hub overlying said portion of the exterior of said attachment fitting.

18. A connector for attaching an auxiliary fixture to the exterior of a length of medical tubing, said connector comprising:

a. an attachment fitting having said fixture secured thereto and having formed therethrough a bore sized to slidably receive a portion of the length of the tubing;

b. a compression recess formed in said attachment fitting having opposed first and second ends, said bore communicating with said first end of compression recess and being disposed in coaxial alignment therewith, said compression recess between said first and said second ends thereof having sidewalls enlarged radially relative to said bore and configured to encircle a portion of the length of the tubing distinct from the portion thereof received in the bore, said first end of said compression recess tapering from said sidewalls thereof to said bore;

c. a resilient, annular gripping member housed in said compression recess and configured to encircle the portion of the tubing therein, said gripping member having a lead end disposed adjacent said first end of said compression recess and a trailing end disposed adjacent said second end of said recess, the edge of said leading end of said gripping member being beveled on the outer radial surface thereof;

d. a locking hub configured for encircling the tubing at said second end of said compression recess and having a compression face projecting into aid compression recess from said second end thereof, said locking hub being movable longitudinally relative said attachment fitting between a disengaged position in which the tubing is slidable relative to said gripping member and an engaged portion in which said compression face bears against and deforms said gripping member to preclude sliding of the tubing relative to said gripping member by urging said gripping member into radial engagement with the portion of the tubing in said compression recess; and e. cooperating means located on opposing portions of said attachment fitting and said locking hub for selectively locking said locking hub in said engaged position thereof, and wherein said cooperating means comprises a retention pin and a retention slot configured to receive said retention pin in said engaged position of said locking hub, said retention pin entering said retention slot due to relative movement between said locking hub and said attachment fitting as said locking hub moves from said disengaged to said engaged position thereof.

19. A connector as recited in claim 18, wherein the juncture between said first end of said compression recess and said bore is a smooth, curving surface.

20. A connector as recited in claim 18, wherein said gripping member is comprised of rubber.

21. A connector as recited in claim 20, wherein said gripping member is comprised of medical grade silicone rubber.

22. A connector as recited in claim 18, wherein said gripping member is comprised of a thermoplastic elastomer.

23. A connector as recited in claim 18, wherein a portion of said gripping member adjacent said first end of said compression recess is extruded into said bore when said locking hub is in said engaged position thereof.

24. A connector as recited in claim 18, wherein the material of which said gripping member is comprised has a Shore A durometer hardness in the range of from about 25 to about 50.

25. A connector as recited in claim 24, wherein the material of which said gripping member is comprised has a Shore A durometer hardness in the range of from about 25 to about 40.

26. A connector as recited in claim 25, wherein the material of which said gripping member is comprised has a Shore A durometer hardness in the range of from about 30 to about 35.

27. A connector as recited in claim 18, wherein the edge of said trailing end of said gripping member is beveled on the outer radial surface thereof.

28. A connector as recited in claim 27, wherein said compression face on said locking hub is inclined relative to the longitudinal axis of said bore at an angle corresponding to the angle of the bevel on the edge of said trailing end of said gripping member.

29. A connector as recited in claim 28, wherein the inner radial surface of at least one end of said gripping member is beveled.

30. A connector as recited in claim 18, wherein the entrance to said retention slot is partially closed by a resilient finger which is temporarily deformed to admit said retention pin to said retention slot.

31. A connector as recited in claim 30, wherein rotation of said locking hub causes said retention pin to enter said retention slot, and entry of said retention pin into said retention slot advances said locking hub longitudinally relative said attachment fitting, thereby to advance said compression face to said compression recess from said second end thereof.

32. A connector as recited in claim 18, wherein said medical tubing comprises an outer lumen tube of a coaxial lumen tube assembly, and a central lumen tube and wherein said fixture comprises a cap portion for said outer lumen.

33. A connector as recited in claim 32, wherein said fixture further comprises:
 a. a tubular side port through said cap portion communicating with the outer lumen tube; and
 b. means for sealingly connecting said cap portion to the outer lumen tube.

34. A connector for effecting selective fluid-tight attachment of a cap portion for an outer lumen tube of a coaxial lumen tube assembly to the outside of an inner lumen tube thereof, the connector comprising:
 a. an attachment fitting secured at one end thereof to the cap portion in coaxial alignment therewith, said cap portion and said attachment fitting having formed therethrough a bore sized to slidably receive a portion of the length of the inner lumen tube;
 b. a compression recess formed in said attachment fitting having opposed first and second ends, said bore communicating with said first end of said compression recess and being disposed in coaxial alignment therewith, said compression recess between said first and second ends thereof having sidewalls enlarged radially relative to said bore and configured to encircle a portion of the length of the inner lumen tube distinct from the portion thereof received in the bore;
 c. a resilient, annular gripping member housed in said compression recess and configured to encircle the portion of the inner lumen tube therein;
 d. a locking hub configured for encircling said inner lumen tube at said second end of said compression recess and having a compression face projecting into said compression recess from said second end thereof, said locking hub being movable longitudinally relative said attachment fitting between a disengaged position in which the inner lumen tube is slidable relative to said gripping member and an engaged position in which said compression face bears against and deforms said gripping member to preclude sliding of the inner lumen tube relative said gripping member by extruding a portion of said gripping member adjacent said first end of said compression recess into said bore and urging said gripping member into radial engagement with the portion of the inner lumen tube in said compression recess;
 e. a retention pin located on said attachment fitting; and
 f. a retention slot formed in said locking hub opposite said retention pin and configured to receive said retention pin in said engaged position of said locking hub, said retention pin entering said retention slot due to relative movement between said locking hub and said attachment fitting as said locking hub moves from said disengaged to said engaged position thereof.

35. A connector as recited in claim 34, wherein said gripping member is comprised of rubber.

36. A connector as recited in claim 35, wherein said gripping member is comprised of medical grade silicone rubber.

37. A connector as recited in claim 34, wherein said gripping member has a lead end disposed adjacent said first end of said compression recess and a trailing end disposed adjacent said second end of said compression recess, and wherein the edge of said lead end of said gripping member is beveled on the outer radial surface thereof.

38. A connector as recited in claim 37, wherein the edge of said trailing end of said gripping member is beveled on the outer radial surface thereof.

39. A connector as recited in claim 33, wherein said gripping member has a lead end disposed adjacent said first end of said compression recess and a trailing end disposed adjacent said second end of said compression recess; wherein the edge of said lead and said trailing ends of said gripping member are beveled on the outer radial surfaces thereof; wherein said first end of said compression recess tapers from said sidewalls thereof to said bore at an angle to the longitudinal axis of said bore corresponding to the angle of the bevel on the outer radial surface of said edge of said lead end of said gripping member; and wherein said compression face on said locking hub is inclined relative to the longitudinal axis of said bore at an angle corresponding to the angle of the bevel on the outer radial surface of said edge of said trailing end of said gripping member.

40. A connector as recited in claim 39, wherein the inner radial surface of at least one end of said gripping member is beveled.

41. A connector as recited in claim 34, wherein said locking hub is secured to said attachment fitting and is capable of rotation about the longitudinal axis of said bore.

42. A connector as recited in claim 34, wherein said first end of said compression recess tapers from said sidewalls thereof to said bore.

43. A connector as recited in claim 42, wherein the juncture between said first end of said compression recess and said bore is a smooth, curving surface.

44. A connector as recited in claim 34, wherein said gripping member is comprised of rubber.

45. A connector as recited in claim 34, wherein the entrance to said retention slot is partially closed by a resilient finger which is temporarily deformed to admit said retention pin to said retention slot.

46. A connector as recited in claim 34, wherein said fixture further comprises:
   a. a tubular side port through said cap portion for communicating with the outer lumen tube; and
   b. means for sealingly connecting said cap portion to the outer lumen tube.

47. A locking connector for effecting a fluid-tight termination of an outer lumen tube against an inner lumen tube of a coaxial lumen tube assembly, said connector comprising:
   a. an attachment fitting having formed therethrough a bore sized to slidably receive a portion of the length of the inner lumen tube;
   b. means for sealingly connecting said fitting to the outer lumen tube;
   c. a compression recess formed in said attachment fitting having opposed first and second ends, said bore communicating with said first end of said compression recess and being disposed in coaxial alignment therewith, said compression recess between said first and said second ends thereof having side walls enlarged radially relative to said bore and configured to encircle a portion of the length of the tubing distinct from the portion thereof received in the bore, said first end of said compression recess tapering from said sidewalls thereof to said bore;
   d. a resilient, annular gripping member housed in said compression recess and configured to encircle the portion of the inner lumen therein, said gripping member having a lead end disposed adjacent said first end of said compression recess and a trailing end disposed adjacent said second end of said recess, the edge of said leading edge of said gripping member being beveled on the outer radial surface thereof;
   e. a locking hub configured for encircling a portion of the length of said inner lumen tube at said second end of said compression recess and having a compression face projecting into said compression recess from said second end thereof, said locking hub being movable longitudinally relative said attachment fitting between a disengaged position in which the inner lumen tube is slidable relative to said gripping member and an engaged position in which said compression face bears against and deforms said gripping member to prelude sliding of the inner lumen tube relative t said gripping member by urging said gripping member into radial engagement with the portion of the inner lumen tube in said compression recess;
   f. a retention pin located on the exterior of said attachment fitting; and
   g. a retention slot formed in a sleeve of said locking hub overlying said retention pin, said retention slot being configured to receive said retention pin in said engaged position of said locking hub due to rotation of said locking hub relative said attachment fitting, entry of said retention pin thereinto causing longitudinal movement of said locking hub parallel to the longitudinal axis of said bore in a direction that advances said compression face into said compression recess.

48. A connector as recited in claim 47, wherein said means for sealingly connecting said fitting to said outer lumen tube comprises a portion of a luer lock connector.

49. A connector as recited in claim 47, wherein the material of which said gripping member is comprised has a Shore A durometer hardness in the range of from about 25 to about 40.

50. A connector as recited in claim 49, wherein the material of which said gripping member is comprised has a Shore A durometer hardness in the range of from about 30 to about 35.

51. A connector as recited in claim 47, wherein said gripping member is comprised of medical grade silicone rubber.

52. A connector as recited in claim 47, wherein said gripping member is comprised of a thermoplastic elastomer.

53. A connector as recited in claim 47, wherein a portion of said gripping member adjacent said first end of said compression recess is extruded into said bore when said locking hub is in said engaged position thereof.

54. A connector as recited in claim 47, wherein the edge of said trailing end of said gripping member is beveled on the outer radial surface thereof.

55. A connector as recited in claim 54, wherein the inner radial surface of at least one end of said gripping member is beveled.

56. A connector as recited in claim 54, wherein said first end of said compression recess tapers from said sidewalls thereof to said bore at an angle to the longitudinal axis of said bore corresponding to the angle of said bevel at the edge of said leading end of said gripping member; and wherein said compression face on said locking hub is inclined at an angle to the longitudinal axis of said bore corresponding to the angle of the bevel at the edge of said trailing end of said gripping member.

57. A fixture for use with an implantable extrapulmonary blood gas exchange device which communicates when implanted in a patient with extracorporeal support equipment through an inner and an outer lumen tube of a coaxial lumen tube assembly, said fixture comprising:
  a. an attachment fitting having formed therethrough a bore sized to slidably receive a portion of the length of the inner lumen tube;
  b. A cap portion secured to one end of said attachment fitting and sized to mate with the outer lumen tube, said bore extending through said cap;
  c. means for sealingly connecting said cap to the outer lumen tube;
  d. a compression recess formed in said attachment fitting having opposed first and second ends, said bore communicating with said first end of said compression recess and being disposed in coaxial alignment therewith, said compression recess between said first and said second ends thereof having side walls enlarged radially relative to said bore and configure dot encircle a portion of the length of inner lumen tube distinct from the portion thereof received in the bore, said first end of said compression recess tapering from said sidewalls thereof to said bore;
  e. a resilient, annular gripping member housed in said compression recess and configured to encircle the portion of the inner lumen tube therein, said gripping member having a lead end disposed adjacent said first end of said compression recess and a trailing end disposed adjacent said second end of said recess, the edges of said leading and said trailing ends of said gripping member being beveled on the outer radial surfaces thereof;
  f. a locking hub configured for encircling a portion of the length of said inner lumen tube at said second end of said compression recess and having a compression face projecting into said compression recess from said second end thereof, said locking hub being movable longitudinally relative said attachment fitting between a disengaged position in which the inner lumen tube is slidable relative to said gripping member and an engaged position in which said compression face bears against and deforms said gripping member to prelude sliding of the inner lumen tube relative said gripping member by urging said gripping member into radial engagement with the portion of the inner lumen tube in said compression recess; and
  g. cooperating means located on opposing portions of said attachment fitting and said locking hub for selecting locking said locking hub in said engaged position thereof and wherein said cooperating means comprises a retention pin located on said attachment fitting and a retention slot formed in said locking hub opposite said retention pin and configured to receive said retention pin in said engaged position of said locking hub due to relative movement between said locking hub and said attachment fitting.

58. A fixture as recited in claim 57, wherein said means for sealingly connecting said cap portion to said outer lumen tube comprises a portion of a luer lock connector.

59. A fixture as recited in claim 57, wherein a portion of said gripping member adjacent said first end of said compression recess is extruded into said bore when said locking hub is in said engaged position thereof.

60. A fixture as recited in claim 59, wherein said gripping member is comprised of rubber.

61. A fixture as recited in claim 60, wherein the material of which said gripping member is comprised has a Shore A durometer hardness in the range of from about 30 to about 35.

62. A fixture as recited in claim 59, wherein the inner radial surface of at least one end of said gripping member is beveled.

63. A fixture as recited in claim 57 wherein said locking hub is secured to said attachment fitting and is capable of rotation about the longitudinal axis of said bore.

64. A fixture as recited in claim 62, wherein the inner radial surface of at least one end of said gripping member is beveled.

65. A fixture as recited in claim 57 wherein the entrance to said retention slot is partially closed by a resilient finger which is temporarily deformed to admit said retention pin to said retention slot.

66. A method for selectively attaching a fixture to the exterior of a length of medical tubing, said method comprising the steps:
  a. inserting an annular gripping member into a compression recess formed in an attachment fitting, said compression recess being coaxially aligned and communicating at one end thereof with a bore through said attachment fitting;
  b. slidably disposing a portion of the length of the tubing in said bore, a portion of the length of the tubing distinct from the portion thereof received in the bore being encircled by said gripping member;
  c. installing a locking hub encircling the tubing at the end of said compression recess opposite said bore, said locking hub having a compression face extending into said compression recess from the end thereof opposite said bore;
  d. longitudinally advancing said locking hub toward said attachment fitting to bring said compression face to bear against and deform said gripping member, thereby to urge said gripping member into radial engagement with the portion of the inner lumen tube in said compression recess;
  e. positively securing said locking hub in position with said compression face deforming said gripping member and wherein said step of positively securing comprises the step of entering a retention pin on said attachment fitting into a retention slot on said locking hub by effecting relative movement of said locking hub and said attachment fitting; and
  f. attaching the fixture to said attachment fitting.

67. A method as recited in claim 66, wherein said step of entering comprises the steps:
  a. rotating said locking hub relative to said attachment fitting; and
  b. advancing said locking hub toward said attachment fitting in a direction parallel to the longitudinal axis thereof.

68. A method as recited in claim 66, wherein a portion of said gripping member adjacent said bore is extruded into said bore when said gripping member is deformed by said compression face.

* * * * *

UNITED STATES PATENT AND TRADEMARK OFFICE
CERTIFICATE OF CORRECTION

PATENT NO. : 5,125,915

DATED : June 30, 1992

INVENTOR(S) : GAYLORD L. BERRY et al.

Page 1 of 2

It is certified that error appears in the above-identified patent and that said Letters Patent is hereby corrected as shown below:

Title page, item [57]
    Abstract, column 2, line 12, after "into" insert --the--
    Column 1, line 22, "an" should be --and--
    Column 1, line 25, "bound are" should be --are bound--
    Column 2, line 39, "are" should be --is--
    Column 2, line 38, after "as" insert --that which--
    Column 3, line 60, after "and" insert --the--
    Column 4, line 15, after "locking" insert --hub is movable--
    Column 4, line 16, delete "hub is movable"
    Column 5, line 46, "become" should be --becomes--
    Column 6, line 54, "hubs 64" should be --hub 64--
    Column 7, line 33, "engagements is" should be --engagement is--

Column 8, line 47, delete "toward the end of precluding" and insert --so as to preclude--
    Column 9, line 11, delete second occurrence of "of"
    Column 9, line 65, "," should be --;--
    Column 10, line 4, after "engagement" insert --on--
    Column 12, line 22, after "on" insert --a--
    Column 12, line 54, "aid" should be --said--
    Column 16, line 15, "t" should be --to--

UNITED STATES PATENT AND TRADEMARK OFFICE
CERTIFICATE OF CORRECTION

PATENT NO. : 5,125,915

DATED : June 30, 1992

INVENTOR(S) : GAYLORD L. BERRY et al.

It is certified that error appears in the above-indentified patent and that said Letters Patent is hereby corrected as shown below:

Column 17, line 53, "selecting" should be --selectively--.

Signed and Sealed this

Ninth Day of November, 1993

Attest:

BRUCE LEHMAN

Attesting Officer

Commissioner of Patents and Trademarks